US00PP29883P3

(12) United States Plant Patent

Maillard et al.

(10) Patent No.: US PP29,883 P3

(45) Date of Patent: Nov. 27, 2018

(54) APRICOT TREE NAMED 'APRICANDY'

(50) Latin Name: ***Prunus armeniaca* L.**
Varietal Denomination: APRICANDY

(71) Applicant: AGRO SELECTIONS FRUITS, Elne (FR)

(72) Inventors: Arsene Maillard, Elne (FR); Laurence Maillard, Elne (FR)

(73) Assignee: AGRO SELECTIONS FRUITS, Elne (FR)

( * ) Notice: Subject to any disclaimer, the term of this patent is extended or adjusted under 35 U.S.C. 154(b) by 0 days.

(21) Appl. No.: 15/732,472

(22) Filed: Nov. 17, 2017

(65) Prior Publication Data

US 2018/0153065 P1 May 31, 2018

(30) Foreign Application Priority Data

Nov. 25, 2016 (QZ) ..... PBR 2016/2949

(51) Int. Cl.
*A01H 5/08* (2018.01)
*A01H 6/74* (2018.01)

(52) U.S. Cl.
USPC ..... Plt./186
CPC ..... *A01H 6/7436* (2018.05); *A01H 5/08* (2013.01)

(58) Field of Classification Search
USPC ..... Plt./186
See application file for complete search history.

*Primary Examiner* — Annette H Para

(74) *Attorney, Agent, or Firm* — Westerman, Hattori, Daniels & Adrian, LLP

(57) ABSTRACT

A new and distinct variety of apricot tree, denominated 'APRICANDY', characterized by its self-fertility and none susceptibility to pests and diseases and by fruits of very good firmness, of very long shelf life without alteration after harvesting, and with an orange flesh, of high eating quality, aromatic and with a high level of sugar, and with an attractive luminous purple red skin on an orange background.

4 Drawing Sheets

Botanical classification: *Prunus armeniaca* L.

Variety denomination: 'APRICANDY'.

This application claims priority of Community plant variety right No. 2016/2949 filed on Nov. 25, 2016, which is hereby incorporated by reference in its entirety.

BACKGROUND OF THE NEW VARIETY

The present invention relates to a new and distinct variety of apricot tree, *Prunus armeniaca* L., which has been given the variety denomination 'APRICANDY'. This new tree produces fruit with a long shelf life without alteration after harvesting, very good eating quality, and orange flesh fruit for fresh market in July in the Pyrénées-Orientales departement, France.

Contrast is made to 'APRINEW' (U.S. Plant Pat. No. 25,630), an apricot tree, for reliable description.

'APRICANDY' is a promising candidate for commercial success in that it has very attractive fruits with long shelf life without alteration after harvesting. This new variety results from our plant-breeding program aimed at obtaining self-pollinating apricot trees producing fruits of sweet and very aromatic taste, with an attractive orange skin covered by an appealing purple red blush. One of our main concerns is also the production of new varieties producing fruits having a long shelf life after harvesting, in order to facilitate long distance shipping. Our final purpose is the production of a range of new apricot tree varieties differing by their time of maturity, while producing fruits of very similar characteristics, in order to provide markets with almost indistinguishable fruits during the whole period of production of apricot.

ORIGIN OF THE VARIETY

The 'APRICANDY' apricot tree originated in a cultivated area of the south of France, in the Pyrénées-Orientales departement, where it was tested.

This place is under a Mediterranean climate (a temperate area), on the Mediterranean coastline. Winters are gentle and summers warm and dry. The amount of days with temperatures below 7° Celsius can vary between 600 and 1200 hours per year. The place is sunny, with 2400 to 2800 hours of sunny days per year on average. The prevailing wind is called 'Tramontane': it dries the air, clears the sky from clouds, but its intensity can be strong and affect the harvest, fruit quantity and/or quality. Marine moisture does not affect the place. Precipitations are irregular through the year and from one year to another. The amount of rainy days does not exceed 80 days per year, and are mostly found in Spring and Autumn. In May and October, very intense precipitations occasionally happen. Summer is dry with a few thunderstorms.

The 'APRICANDY' variety resulted from a controlled cross between the 'ASFCOT0201' (U.S. Plant Pat. No. 24,093) which was used as the seed parent and the 'SELECTION ASF0408' (not patented) which was used as the pollen parent.

The 'APRICANDY' variety was propagated by grafting on a 'FRANC INRA® MONTCLAR' (non patented) rootstock trees. It has been determined to have unique tree and fruit characteristics making it worthy for commercial fresh fruit production. There are no known effects of the standard rootstock trees set forth above on the scion cultivar. Asexually propagated plants remained true to the original tree and all characteristics of the tree and the fruit were transmitted. The plant was reproduced asexually by us in Les Régalines, Route d'Alenya, La Prade de Mousseillous, 66200 ELNE, Pyrénées-Orientales, France. More particularly, the plant was reproduced by grafting.

SUMMARY OF THE VARIETY

The new and distinct variety of apricot tree blooms generally at the end of March in the Pyrénées-Orientales departement, France. More particularly, the blooming period generally starts March 21$^{st}$. However, it was observed that its early date of blooming seems to be highly dependant on climatic conditions.

The first fruit of 'APRICANDY' apricot tree ripens early or mid-July, generally about 5 to 7 days later than the similar apricot variety named 'APRINEW' (U.S. Plant Pat. No. 25,630). However, it was observed that its early date of maturity seems to be highly dependant on climatic conditions.

DESCRIPTION OF THE DRAWINGS

In the accompanying drawing, which are as nearly true as it is reasonably possible to make in a color illustration of this type.

Figure 1:
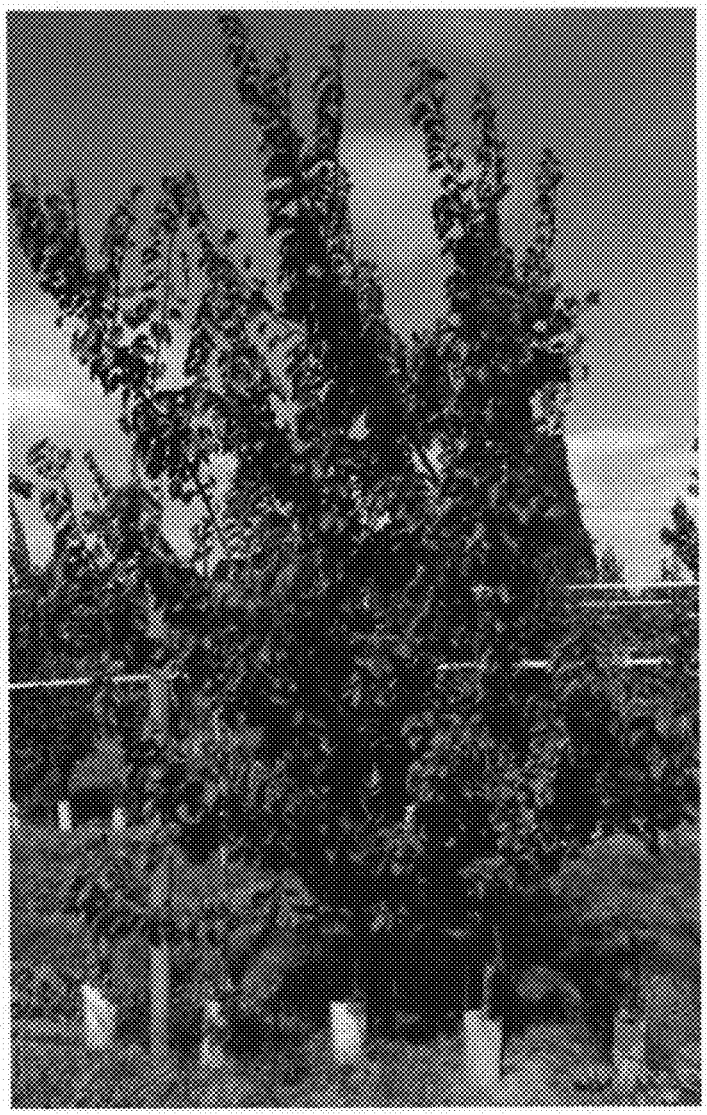
FIG. 1 is a color photograph, which shows a view of an apricot tree of the new variety in orchard, bearing fruits.
Figure 2:
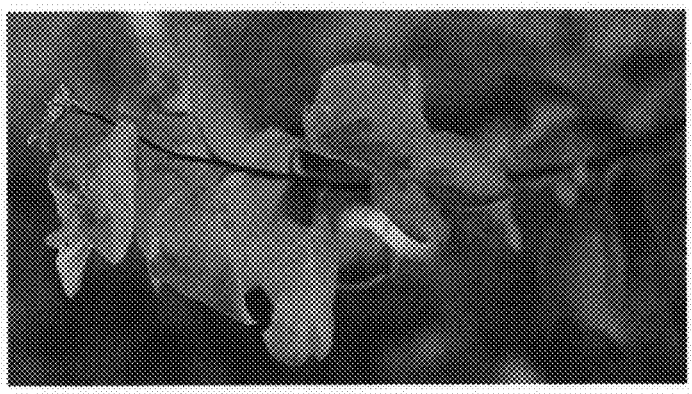
FIG. 2 is a color photograph, which shows a closest view of a current season shoot of the new variety in orchard.
Figure 3:
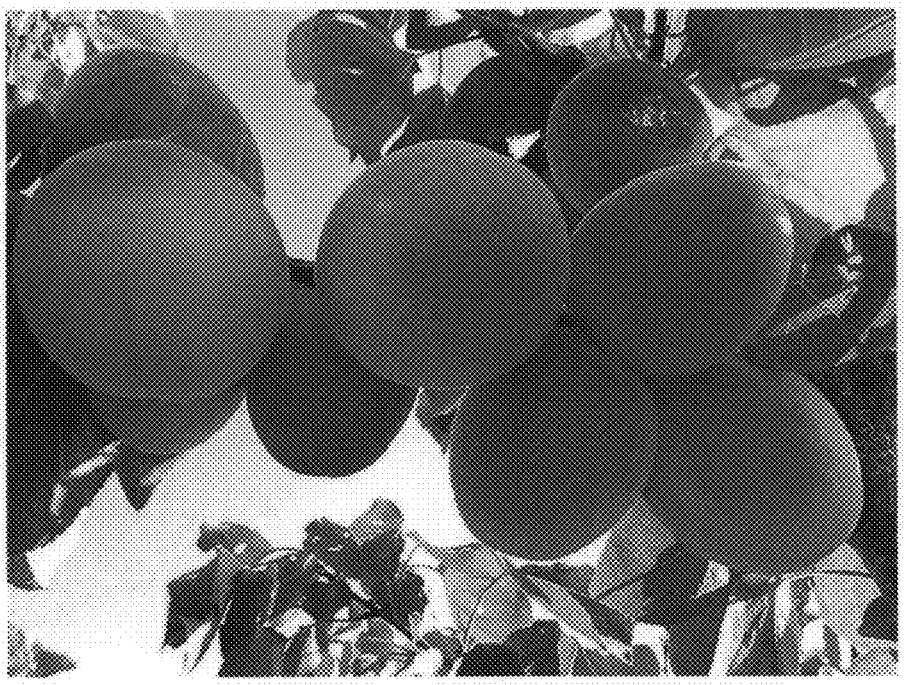
FIG. 3 is a color photograph, which shows a closest view of branches of the new variety in orchard, bearing fruits.
Figure 4:
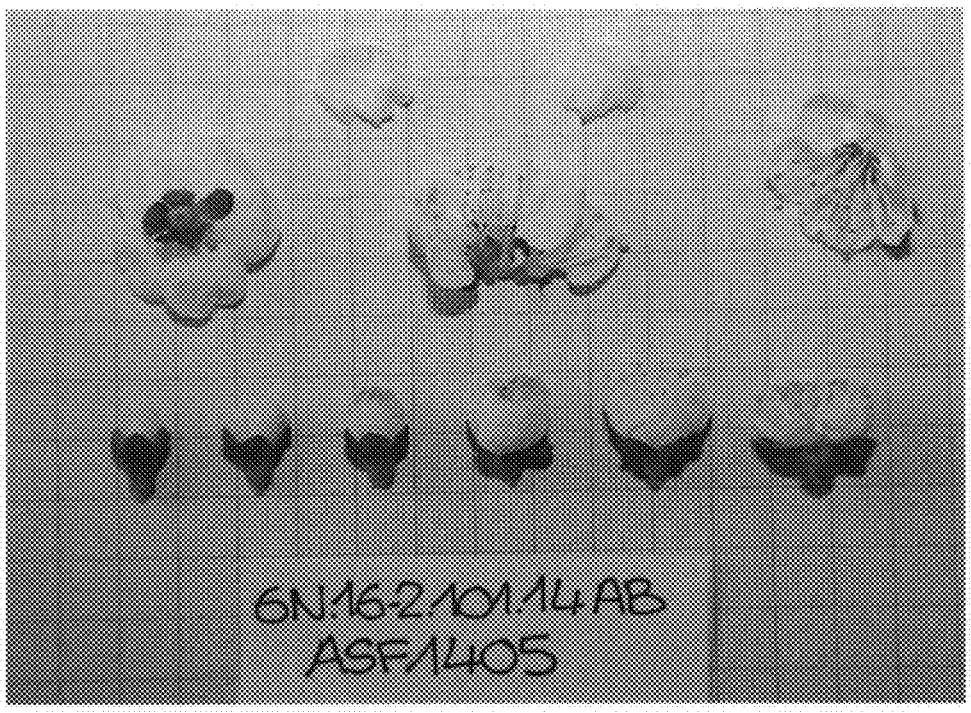
FIG. 4 is a color photograph with reverse and side views of flowers of the new variety, and, with petals removed, reproductive organs of the new variety.
Figure 5:
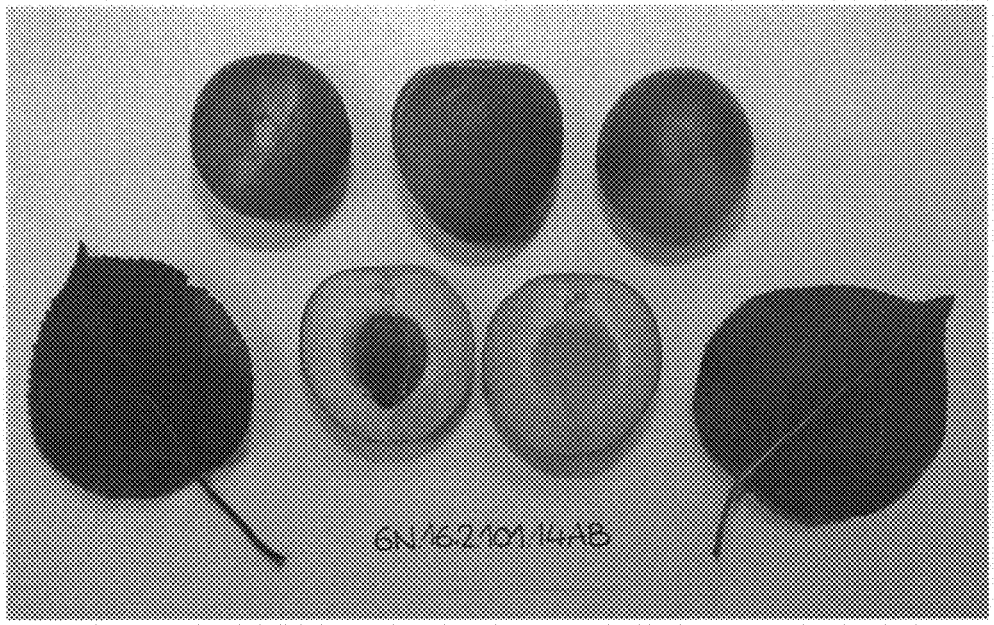
FIG. 5 is a color photograph, which shows three whole fruits and leaves of the new variety, and a fourth fruit, cut in half, with the stone left in one of the halves for depicting the fruit flesh the stone and the stone cavity of the new variety, as well as the leaves of the variety.
Figure 6:
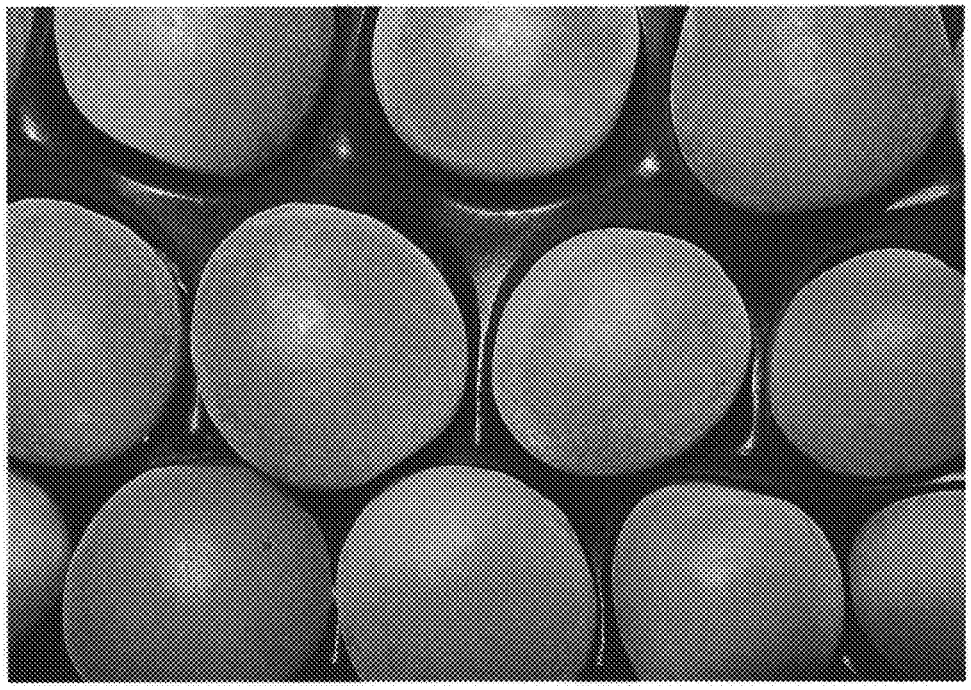
FIG. 6 is a color photograph showing a close view of typical specimens of the new variety 'APRICANDY' at ripening time.
Figure 7:
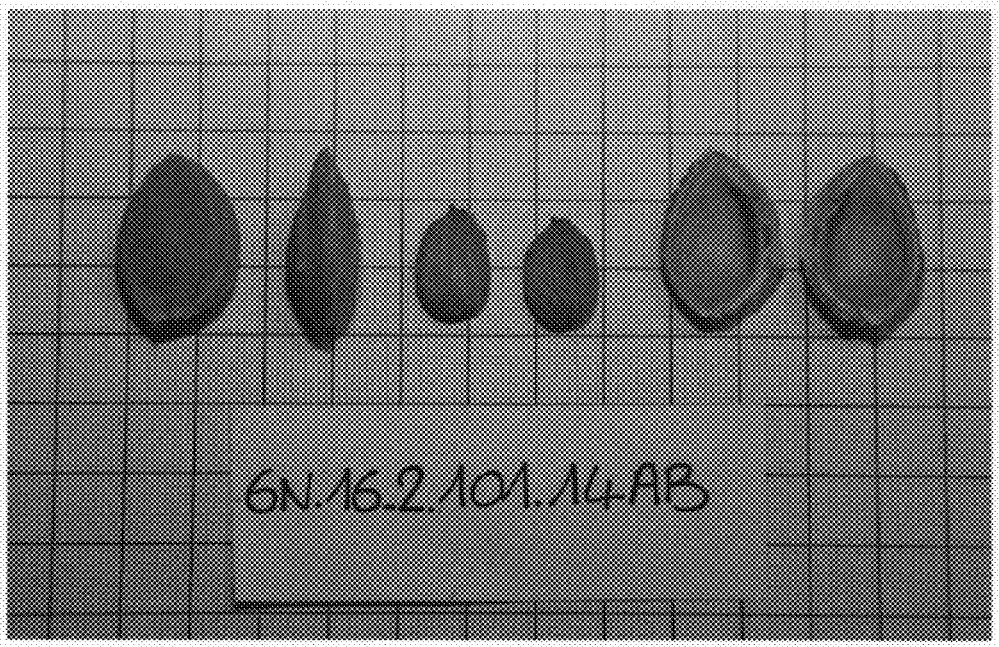
FIG. 7 is a color photograph showing different view of two whole stones of the new variety, and a third stone cut in half for depicting the kernel of the stone.

Due to chemical development, processing and printing, the leaves and fruit depicted in these photographs may or may not be accurate when compared to the actual botanical specimen.

DETAILED BOTANICAL DESCRIPTION

The tree, flowers, and fruit may vary in slight detail due to variations in soil type, cultural practices, and climatic condition. The potential for commercial production of fresh fruit by 'APRICANDY' is high, due to fruit very long shelf life without alteration after harvesting.

Trees are medium vigorous and medium stature in a naturally semi-upright out aspect. The time of beginning of flowering is considered medium; flowering begins at the end of the month of March. The flower petals are medium and colored in white or in an extremely pale pink. Leaf glands are present and round. Time of maturity for consumption is considered medium, namely at the beginning of July or mid-July. The fruit flesh is considered orange. The fruit skin is medium thick and colored with a purple red blush on an orange background. The stone is medium size. Fruit taste is very aromatic and with a high level of sugar.

Compared to 'APRINEW' (U.S. Plant Pat. No. 25,630) apricot tree, 'APRICANDY' variety ripens approximately 5 to 7 days later, as set forth above. On the contrary, 'APRICANDY' variety has an earlier blooming time, compared to 'APRINEW'.

Moreover, the 'APRICANDY' variety produces very attractive fruits, with a purple red blush covering between 80 and 85% of the fruit skin, on an orange background. In comparison, 'APRINEW' apricot tree produces fruits with a blush covering 25 to 50% of the skin, on an orange background.

The fruit flesh of 'APRICANDY' has a very good taste, very sugary, between 18 and 25 brix, very aromatic, and consequently more sugary. In comparison, the fruits of the 'APRINEW' variety have a good taste, sugary, with between 16 and 18 brix and aromatic, so the taste is less sugary than the taste of the 'APRICANDY' fruits.

Compared to its seed parent 'ASFCOT0201' (U.S. Plant Pat. No. 24,093), 'APRICANDY' is a self pollinating variety, so 'APRICANDY' does not require any pollinator. On the contrary, 'ASFCOT0201' (U.S. Plant Pat. No. 24,093) need to be pollinated by other varieties in order to get yearly production.

Moreover, compared to its seed parent 'ASFCOT0201' (U.S. Plant Pat. No. 24,093) the 'APRICANDY' variety ripens approximately 5 to 9 days later and, 'ASFCOT0201' variety has an earlier blooming time, compared to 'APRICANDY'.

Compared to its pollen parent 'ASF0408', both are self-pollinating varieties. However, 'ASF0408' variety ripens approximately 10 days before 'APRICANDY' variety.

DETAILED DESCRIPTION

Referring more specifically to the pomological details of this new and distinct variety of apricot tree, the following was observed on trees during the 2014, 2015 and 2017 growing seasons under the ecological conditions prevailing at the orchards located near the town of Elne, Pyrénées-Orientales departement, France. All observations have been done on rootstock cultivars. Used rootstocks were 'FRANC INRA® MONTCLAR' (non patented) trees. All major color code designations are by reference to The R.H.S. Color Chart (Fourth Edition) provided by The Royal Horticultural Society of Great Britain.

Tree:

Size:

*Generally.*—Considered medium as compared to other common commercial apricot cultivars. Trees reach about 250 cm during the first growing season. Trees were pruned during each following season to a height of approximately 250 cm and to a diameter of 200 cm.

*Spread.*—Approximately 200 cm. The whole orchard was oriented to a central leader organization, with tree lines spaced of 4.0 meters and trees spaced of 1.0 meter in a same tree line.

*Vigor.*—Considered medium vigorous. Current season shoots growth could reach 100 cm. During the first year of growth, trees growth reaches 250 cm. In the second and following seasons, the size of trees is reduced to 250 cm by pruning. However, these characteristics are dependant on soils fertility, cultural practices, and prevailing climatic conditions.

*Productivity.*—The productivity is considered good to very good, and regular. Fruit set is spaced by thinning to develop the remaining fruit into the desired market sized fruit. Because of the fruit size, the new variety only requires a medium thinning for the tree valorisation. Thinning was necessary every year during the years of observation. The number of the fruit set varies with the prevailing climatic conditions and cultural practices employed during the bloom period, and is therefore not distinctive of the present variety.

*Bearer.*—Very regular. No alternate bearing was observed.

*Form.*—The 'APRICANDY' variety has a naturally semi-spreading shape.

*Density.*—Considered highly dense, in order to obtain and observe fruits more quickly.

*Fertility.*—The 'APRICANDY' variety is considered autofertile. A genetic analysis has been done during year 2015 in order to confirm the autofertile characteristic of 'APRICANDY' variety. The alleles of 'APRICANDY' variety are S1 and S5.

*Hardiness.*—The present tree was grown and evaluated in France. The variety appears to be hardy under the central Pyrénées-Orientales departement typical climatic conditions. Experimentations on different sites with winter chilling requirement comprised between 350 hours and 1200 hours showed a good behaviour of the tree in all cases. The tree also seems to have a good resistance to frosty springtime weather.

Trunk:

*Diameter.*—Approximately 7.5 centimeters to 8.0 centimeters in diameter when measured at a distance of approximately 20.0 centimeters above the soil level.

*Bark texture.*—Considered rough with lenticels.

*Bark coloration.*—The bark has mostly a grey to a brown color (RHS Grey 201 A to RHS Grey 201 B to RHS Brown 200 B).

Lenticels:

*Lenticel color.*—A beige color (RHS Greyed Orange 164 D).

*Density.*—The number of lenticels is approximately 2 lenticels per $cm^2$.

*Size.*—Lenticels are approximately 1.7 to 2.0 millimeters in width and 3.2 to 5.0 millimeters long.

Branches:

*Size.*—The branches are pruned every year to approximately 1.0 meter in length.

*Diameter.*—Average as compared to other apricot varieties. The current season shoots have a diameter of about 4.0 to 6.0 millimeters, and mature branches have a diameter of about 8.5 to 10.0 millimeters.

*Surface texture.*—Current season shoots have a smooth texture. Mature branches are medium rough. Roughness increases with trees age. Wood which is several years old has furrowed appearance.

*Crotch angles.*—The crotch angles are generally 45 degrees from the trunk axis, for current season shoots. At maturity, the crotch angle increases with fruits weight, until 60 degrees. This particular characteristic is not considered distinctive of the variety, however.

Current season shoots:

*Internode length.*—Generally 12.0 millimeters.

*Color of current season's shoots.*—Considered orange brown (RHS Greyed Orange 175 A) on lower part of new shoot tips, whereas the upper part is darker and colored in brown-purple (RHS Greyed Purple 185 A). The current season's shoots color evolves and turns to mature branches color when aging.

Mature branches:

*Internode length.*—Generally 18.0 millimeters.

*Color of mature branches.*—Brown (RHS Greyed Orange 166 A).

*Vigor.*—Considered spread as for all the apricot varieties.

Lenticels:

*Density.*—Lenticels are present, just as on the trunk, especially on mature branches. More particularly, 2 lenticels appear per $cm^2$ on mature branches.

*Size.*—Considered small, and slightly smaller than trunk's lenticels, they are approximately 2.0 to 3.0 millimeters wide and 1.2 to 1.6 millimeters long.

*Color.*—Considered beige color (RHS Greyed Yellow 162 C or RHS Greyed Yellow 162 D).

*Form.*—Stretched.

Leaves:

*Size.*—Considered medium for the species.

*Leaf length.*—The leave's length is between 104.0 and 123.0 millimeters with leaf petiole.

*Leaf width.*—The leave's width is between 70.0 and 87.0 millimeters.

*Leaf form in cross section.*—Concave.

*Leaf form.*—Almost circular.

*Leaf tip form.*—Acuminate.

*Leaf base form.*—Generally truncate.

*Leaf margins.*—Considered dentate.

*Thickness.*—Medium.

*Upper surface texture.*—Smooth.

*Lower surface texture.*—Smooth.

Leaf color:

*Upper leaf surface.*—The color of the upper leaf surface is green (RHS Yellow Green 147 A or RHS Green 137 A).

*Lower surface.*—A lighter green than the upper leaf surface color. The lower surface of leaves is RHS Yellow Green 146 A or RHS Yellow Green 147 B.

*Leaf venation.*—Pinnately veined.

Mid-vein:

*Thickness.*—Approximately 1.5 to 2.0 millimeters when measured at the base of the leaf.

*Color.*—Red purple (RHS Red Purple Group 59 B).

*Other veins color.*—Light green (RHS Yellow Green N 144 A or RHS Green Group 143 B).

*Uniformity.*—Leaves are of medium size and generally found alone. No stipules are generally found.

Leaf petioles:

*Size.*—Generally long.

*Length.*—The leaf petiole length is between 30.0 and 46.0 millimeters.

*Diameter.*—Approximately between 1.5 millimeters to 2.0 millimeters.

*Surface.*—Smooth to slightly ribbed.

Petioles colour:

*Upper petiole surface.*—Depending on climatic conditions and sunlight exposure, the anthocyanic coloration on petiole's upper surface is generally considered red (RHS Red Group 53 B) to purple red (RHS Red Purple 59 B or RHS Greyed Purple 183 A).

*Lower petiole surface.*—Light green (RHS Yellow Green 145 A).

Leaf glands:

*Size.*—Considered small.

*Length.*—Approximately 0.5 millimeter to 1.5 millimeters.

*Width.*—Approximately 0.5 millimeter to 1.5 millimeters.

*Number.*—Between 2 and 3 glands per leaf.

*Type.*—Circular.

*Margins.*—Smooth and regular.

*Position.*—Alternate between upper portion of petiole and lower portion of leaf blade.

*Color.*—Generally grey orange (RHS Greyed Orange Group 165 A).

Leaf stipules:

*Generally.*—No leaf stipules were observed.

Flowers:

Flower buds:

*Generally.*—At pre-floral stage of development, the floral buds are conic in form with a very rounded tip (ball shaped). Their form is evolving until blooming, with variables dimensions. At the pre-floral stage, the size of flower buds is 7.0 to 9.0 millimeters wide and approximately 13.0 to 16.0 millimeters long. Just before blooming, floral buds are approximately 13.0 millimeters wide and approximately 20.0 millimeters long. Generally, a bud is found alone or in group of two or three buds.

*Color.*—This characteristic is dependent upon the proximity to bloom. At pre-floral stage of development, the bottom of the flowers buds, formed by the sepals, is of purple-brown color (RHS Greyed Purple 184 B to RHS Greyed Purple 184 C); the corolla, formed by the petals, is generally of pale pink color (RHS Red 56 C or RHS Red Purple 69 B or RHS Red Purple 69 C or RHS Red Purple 62 C or RHS Red Purple 62 D). The petal color generally evolves until the end of the blooming period, becoming whiter.

*Hardiness.*—The buds are considered hardy under typical central Pyrénées-Orientales departement climatic conditions. No winter injury was noted during the last several years of evaluation in the central Pyrénées-Orientales departement, with winter temperatures as low as −10 degrees Celsius in January. The current variety has not been intentionally subjected to drought or heat stress, but the variety showed a very good resistance in orchard to temperatures up to 42 degrees Celsius with an average temperature between 28 and 30 degrees Celsius during 3 weeks in summer.

*Date of bloom.*—During March.

*First bloom.*—The first bloom was observed on Mar. 21, 2015.

*Petal fall.*—Mar. 31, 2015.

*Blooming time.*—Considered medium season in relative comparison to other commercial apricot cultivars grown in the Pyrénées-Orientales departement, France. Thus, the first blooming time was from March 21$^{st}$ until Mar. 31, 2015, then from March 21$^{st}$ until Apr. 2, 2016 and then from March 6$^{th}$ until Mar. 17, 2017.

*Duration of bloom.*—Medium, approximately between 11 and 13 days.

Spurs:

*Lenticels.*—A few lenticels are present, more particularly between 2 to 7 per linear centimeter, but their number may vary with environmental conditions.

*Form.*—Ovate.

*Length.*—Approximately 2.0 millimeters.

*Width.*—Approximately 1.5 millimeters.

*Color.*—Orange grey (RHS Greyed Orange 165 A).

*Flower type.*—The variety is considered to have a showy type of flower.

*Flower size.*—Medium. Flower diameter at full bloom is approximately 26.0 to 30.0 millimeters.

*Bloom quantity.*—Considered abundant to very abundant, between 50 and 55 flowers per linear meter. Flowers are generally found in bunches.

*Flower bud frequency.*—Generally 1 flower bud or several flower buds per groups of 2 to 3.

Petal size:

*Generally.*—Medium.

*Length.*—Generally between 13.0 and 16.0 millimeters.

*Width.*—Generally between 14.0 and 18.0 millimeters.

*Petal form.*—Round-shaped.

*Petal count.*—Generally 5, and sometimes more than 5, overlapping.

*Petal texture.*—Smooth, soft and glabrous. Sometimes, petals are slightly creased.

*Petal color.*—At the stage F of blooming, when the flower is fully opened, both surfaces of petals are colored with a white (RHS White Group N 155 B or RHS White Group N 155 C) to a very light pink (RHS Red Purple 69 D) color.

*Fragrance.*—Sweet.

Petal claw:

*Form.*—Narrow.

*Length.*—About 1.0 to 1.5 millimeters.

*Width.*—About 1.0 millimeter at the base.

*Color.*—Generally the claw is colored like petal color (RHS White Group N 155 B to RHS White Group N 155 C or RHS Red Purple 69 D), sometimes slightly darker than the petal color (RHS Red Purple 73 C or RHS Red Purple 73 D) with a small pink tip near the petal attach (RHS Red 54 A).

*Petal margins form.*—Smooth and sometimes slightly wavy especially near the base.

*Petal base.*—Narrow at point of attachment.

*Petal apex.*—Wide-dome shaped or round.

Petal peduncle:

*Length.*—Approximately 2.0 to 4.0 millimeters.

*Diameter.*—Approximately 2.0 to 2.5 millimeters.

*Color.*—Generally light green (RHS Yellow Green 145 B or RHS Yellow Green C) and covered with small overlapping scales colored purple brown (RHS Greyed Red 178 A or RHS Greyed Red 178 B) to orange brown (RHS Greyed Orange 175 A or RHS Greyed Orange 175 B).

Sepals:

*Generally.*—Star shaped around the corolla base.

*Size.*—Considered medium.

*Length.*—Approximately between 5.0 and 7.0 millimeters.

*Width.*—Approximately between 4.0 and 6.0 millimeters.

*Sepal count.*—Generally 5, sometimes more, until 8 sepals.

*Form.*—Triangular, with a slightly pointed apex, or elliptic.

*Margins.*—Smooth.

*Color.*—The outer surface of the sepals is considered of purple color (RHS Greyed Purple 184 B or RHS Greyed Purple 184 C or RHS Greyed Purple 185 A or RHS Greyed Purple 185 B or RHS Greyed Purple 185 C) and light green at their base (RHS Yellow Green 151 B or RHS Yellow Green 151 C or RHS Yellow Green 150 C). The inner surface of the sepals is colored in a lighter purple than the outer surface (RHS Greyed Purple 181 A or RHS Greyed Purple 181 B).

*Surface texture.*—Smooth.

Stamens:

*Average number of stamens per flower.*—Between 29 and 39.

*Size.*—Approximately between 11.0 and 16.0 millimeters in length, generally higher than pistil's length. Generally, stamens are smaller than petals and sometimes at the same level.

*Color.*—White (RHS White 155 D or RHS White Group 155 B or RHS White Group 155 C).

Anthers:

*Size.*—Generally small in length.

*Shape.*—Round.

*Color.*—Yellow (RHS Yellow 12 A) to orange yellow (RHS Yellow Orange 16 A to RHS Yellow Orange 16 B), which may evolve with maturity.

Pistil:

*Number.*—Usually 1.

*Length.*—Approximately 13.0 to 14.0 millimeters, or 17.0 to 19.0 millimeters including the ovary. The pistil's length is smaller than stamen's length.

*Color.*—Considered very pale green (RHS Yellow Green 150 D or RHS Yellow Green 145 D) to white (RHS White Group 155 C).

Pollen:

*Pollen production.*—Pollen production is considered good. The variety is self-fertile.

*Color.*—Yellow (RHS Yellow 11 A) to orange yellow color (RHS Yellow Orange 16 A to RHS Yellow Orange 16 B).

Calyx:

*Internal surface texture.*—Smooth and glabrous.

*Color.*—The inner surface of the calyx, namely the flower receptacle, is considered yellow orange (RHS Yellow 11 A or RHS Orange N 25 A) whereas the outer surface is purple (RHS Greyed Purple 184 B or RHS Greyed Purple 184 C or RHS Greyed Purple 185 A or RHS Greyed Purple 185 B or RHS Greyed Purple 185 C) becoming slightly lighter near calyx base and light green near the peduncle (RHS Yellow Green 151 B or RHS Yellow Green 151 C or RHS Yellow Green 150 C).

Ovary:

*Pubescence.*—Present.

*Height.*—Between 2.0 and 2.5 millimeters.

*Diameter.*—Between 2.0 and 2.5 millimeters.

*Color.*—Light green (RHS Yellow Green 145 A).

Stigma:

*Position compared to anthers.*—The stigma is below the anthers, or at the same level.

*Diameter.*—Approximately 1.0 millimeter.

*Color.*—Yellow (RHS Yellow 12 A).

Fruit:

*Maturity.*—Considered medium. Generally, fruits become mature during July, more particularly at the beginning of July.

*Date of first picking.*—Jul. 3, 2014.

*Date of last picking.*—The date of harvest varies slightly with the prevailing climatic conditions. The 'APRICANDY' variety has a medium date of picking and a grouped maturity. The maturity is usually grouped within 5 to 7 days and the harvest is generally performed in two runs. The first picking was carry on from July 3$^{rd}$ to Jul. 9, 2014. The next picking times were from July 8$^{th}$ to Jul. 12, 2015, and from July 16$^{th}$ to Jul. 21, 2016 and then from June 27$^{th}$ to Jul. 5, 2017.

Size:

*Generally.*—Considered medium.

*Length.*—Approximately and between 50.0 and 54.0 millimeters.

*Width.*—Approximately between 48.0 and 50.0 millimeters.

*Thickness.*—Approximately between 45.0 and 48.0 millimeters.

*Typical weight.*—Generally between 60.0 and 75.0 grams. This characteristic is high dependent especially upon the prevailing cultural practices, and therefore is not particularly distinctive of the variety.

Fruit form:

*Generally.*—Round and slightly oblong near the apex and at the fruit base. The fruit is considered to be symmetrical.

Suture:

*Generally.*—Very slightly marked, extending from the base to the apex.

*Color.*—The suture has generally a color similar to the whole fruit color. The suture is colored with purple red color (RHS Greyed Purple 185 A or RHS Greyed Purple 187 A or RHS Greyed Purple 187 B).

Ventral surface:

*Form.*—Round.

*Apex.*—Flat.

*Base.*—Straight to slightly retuse.

*Stem cavity.*—Shallow. Average depth of the stem cavity is about 6.0 to 8.0 millimeters. Average width is about 8.0 to 13 millimeters.

Stem:

*Size.*—Generally small and short. Stem length is about 4.0 millimeters. Stem diameter is about 2.5 millimeters.

*Color.*—Stem color is generally green (RHS Yellow Green 145 A or RHS Yellow Green 145 B).

Fruit skin:

*Thickness.*—Considered medium, adherent and resistant.

*Texture.*—Smooth.

*Pubescence.*—Present but very light, almost non-existent.

*Tendency to crack.*—None observed.

Color:

*Blush color.*—This blush color is purple red (RHS Greyed Purple 185 A or RHS Greyed Purple 187 A or RHS Greyed Purple 187 B). The purple red blush covers between 80 and 85% of the fruit skin surface for fruits that are exposed to sunlight. The percentage of the blush on the fruit skin surface can vary, and is generally dependant upon the prevailing conditions under which the fruit was grown.

*Ground color.*—The ground color covers 15 to 20% of the fruit skin surface, and is considered orange (RHS Orange 26 A).

*Adherence to flesh.*—Adherent.

*Taste.*—Moderately acid and sugared.

Flesh:

*Ripens.*—The maturing of the fruit is uniform.

*Texture.*—Fine and firm. Very melting and juicy at end of maturity.

*Fibers.*—Generally none observed.

*Aroma.*—Very present, pronounced.

*Firmness.*—Firm. Holds firmness over the time.

*Eating quality.*—Considered very good and with a high level of sugars.

*Flavor.*—Considered very good. Semi sweet and with a good balance between sugar and acidity. Very aromatic.

*Juice.*—Very juicy. The juiciness increases with maturity.

*Brix.*—Generally superior to 16.0 degrees, between 18.0 and 25.0 degrees. This characteristic varies slightly with the number of fruits per tree, prevailing cultural practices and the surrounding climatic conditions.

*Flesh color.*—Considered medium orange (RHS Orange 23 A or RHS Yellow Orange 23 C).

Stone:

Stone cavity:

*Color.*—The stone cavity shows the same orange color (RHS Orange 23 A or RHS Yellow Orange 23 C) as the flesh color.

*Length.*—Similar to the stone's length.

*Stone type.*—Free, but the stone seems to be slightly attached to the flesh through its base.

*Size.*—Considered medium for the variety. The stone size varies depending upon the tree vigor, crop load and prevailing growing conditions.

*Length.*—Approximately 26.0 to 30.0 millimeters.

*Width.*—Approximately 18.0 to 21.0 millimeters.

*Diameter.*—Approximately 10.0 to 12.0 millimeters.

*Stone form.*—Ovoid.

*Stone form* (*viewed from stem end*).—Ovate flattened.

*Stone form* (*lateral view*).—Oblong.

*Stone base shape.*—Round to slightly concave.

*Stone apex shape.*—Round, generally not pointed.

*Symmetry.*—Symmetric.

Stone surface:

*Surface texture.*—Slightly rough.

*Ridges at stone surface.*—The ridges are present on both sides of the stone. A ridge is generally narrow. The ridges begin at the base and are extending all along the stone length.

*Stone color.*—The color of the dry stone is generally considered a greyed orange (RHS Greyed Orange 165 B or RHS Greyed Orange 164 C).

*Tendency to split.*—Splitting is absent.

Kernel:

*Taste.*—Bitter.

*Size.*—Medium.

*Length.*—Approximately 16.0 to 17.0 millimeters.

*Width.*—Approximately 11.0 to 13.0 millimeters.

*Thickness.*—Approximately 6.0 millimeters.

*Form.*—Ovate.

*Color.*—The kernel skin is a greyed orange (RHS Greyed Orange 164 B or RHS Greyed Orange 164 C or RHS Greyed Orange 165 B). The almond, which is the seed of the kernel, is considered white (RHS White 155 D).

*Use.*—The subject variety 'APRICANDY' is considered to be a apricot tree with a medium season maturity, and which produces fruits that are considered firm, attractively and luminously colored with a high proportion of purple red blush covering the skin surface. Fruits have a balanced taste between acidity and sugar. They are excellent for uncooked or cooked consumption, melting and juicy when at full maturity. Fruits have excellent gustative qualities and are very aromatic. They are also useful for both local markets and very long distance shipping.

*Keeping quality.*—Good. Fruits are well preserved during at least 3 weeks after harvest in a cold atmosphere. Fruits are considered to have a long shelf life after harvesting without alteration.

*Shipping quality.*—Considered good. The fruits of the new apricot variety showed very little skin scarring or flesh bruises in picking, packing and shipping trials.

*Resistance to insects and disease.*—No particular susceptibilities were noted. Under meticulous observations during planting, growing and harvesting of fruits, no particular resistance or sensitivity to plant or fruits diseases were noticed. Any variety, observed during indexing of plant characteristics, with abnormal fungus, bacterial virus or insect sensitivity is destroyed and eliminated from our breeding program. Although the new variety of apricot tree possesses the described characteristics when grown under the ecological conditions prevailing near Elne, Pyrénées-Orientales departement, France, it should be understood that variations of the usual magnitude and characteristics incident to changes in growing conditions, fertilization, pruning, pest control and horticultural management are to be expected.

I claim:

1. A new and distinct variety of apricot tree as illustrated and described, characterized by its self-fertility and none susceptibility to pests and diseases and by fruits of very good firmness, of very long shelf life without alteration after harvesting, and with an orange flesh, of high eating quality, aromatic and with a high level of sugar, and with an attractive luminous purple red skin on an orange background.

* * * * *